(12) United States Patent
Davies et al.

(10) Patent No.: US 7,851,487 B2
(45) Date of Patent: *Dec. 14, 2010

(54) USE OF TETRAHYDROPYRIDINES IN THE TREATMENT OF CENTRAL NERVOUS SYSTEM DISORDERS

(75) Inventors: Huw M. L. Davies, E. Amherst, NY (US); Anil K. Ratty, Singapore (SG)

(73) Assignees: The Research Foundation of State University of New York, Amherst, NY (US); Chakra Biotech Pte Ltd., Singapore (SG)

(*) Notice: Subject to any disclaimer, the term of this patent is extended or adjusted under 35 U.S.C. 154(b) by 588 days.

This patent is subject to a terminal disclaimer.

(21) Appl. No.: 11/716,815

(22) Filed: Mar. 12, 2007

(65) Prior Publication Data

US 2007/0249646 A1 Oct. 25, 2007

Related U.S. Application Data

(60) Provisional application No. 60/781,245, filed on Mar. 10, 2006.

(51) Int. Cl.
| | |
|---|---|
| *A01N 43/40* | (2006.01) |
| *A61K 31/445* | (2006.01) |
| *C07D 211/00* | (2006.01) |
| *C07D 211/30* | (2006.01) |
| *C07D 211/20* | (2006.01) |
| *C07D 295/00* | (2006.01) |

(52) U.S. Cl. .................. 514/317; 546/184; 546/248
(58) Field of Classification Search ................ 514/317; 546/184, 248

See application file for complete search history.

(56) References Cited

U.S. PATENT DOCUMENTS

| | | | |
|---|---|---|---|
| 5,227,385 A | 7/1993 | Caldwell et al. | |
| 5,262,428 A | 11/1993 | Davies et al. | |
| 5,288,872 A | 2/1994 | Davies et al. | |
| 5,342,949 A | 8/1994 | Davies et al. | |
| 5,591,854 A | 1/1997 | Davies | |
| 5,760,055 A | 6/1998 | Davies | |
| 5,763,455 A | 6/1998 | Davies et al. | |
| 5,849,765 A | 12/1998 | Curtis et al. | |
| 6,008,227 A | 12/1999 | Davies et al. | |
| 6,013,242 A | 1/2000 | Davies et al. | |

OTHER PUBLICATIONS

Davidson et. al., The American Journal of Psychiatry, 1996, American Psychiatric Association, vol. 153, issue 10, pp. 1274-1279.*

Kampman et. al., Drug and Alcohol Dependence, 2003, Elsevier Science, vol. 70, pp. 265-273.*

Lieberman et al., The New England Journal of Medicine, 2005, Massachusetts Medical Society, vol. 353, No. 12, pp. 1209-1223.*

Horishita et. al., Anesth. Analg., 2002, International Anesthesia Research Society, vol. 95, pp. 1661-1666.*

Davies et al., Synthesis of methylphenidate analogues and their binding affinities at dopamine and serotonin transport sites. Bioorganic & Medicinal Chemistry Letters 14 (2004) 1799-1802.

Davies et al., New Strategic Reactions for Organic Synthesis: Catalytic Asymmetric C-H Activation α to Nitrogen as a Surrogate for the Mannich Reaction. Journal of the American Chemical Society, 2003, V. 125, No. 21, pp. 6462-6468.

Davies, et al.; Highly Regio-, Diastereo-, and Enantioselective C-H Insertions of Methyl Aryldiazoacetates into Cyclic N-Boc-Protected Amines. Asymmetric Synthesis of Novel $C_2$-Symmetric Amines and *threo*-Methylphenidate; J. American Chemical Society 1999, vol. 121; pp. 6509-6510.

* cited by examiner

*Primary Examiner*—Sreeni Padmanabhan
*Assistant Examiner*—Sarah Pihonak
(74) *Attorney, Agent, or Firm*—Hodgson Russ LLP

(57) ABSTRACT

Disclosed are methods for alleviating symptoms of neuropsychiatric disorders using tetrahydropyridine derivatives bearing aromatic substituents. The method comprises administering to an individual a tetrahydropyridine derivative bearing aromatic substituents in an amount effective to alleviate symptoms of the neuropsychiatric disorder.

17 Claims, 1 Drawing Sheet

| Ar | Rh(II) | yield, % | de, % | ee, % | product |
|---|---|---|---|---|---|
| 4-BrC6H4 | Rh2(S-DOSP)4 | 70 | 82 | 95 | (2S,2'R)-4b |
|  | Rh2(R-DOSP)4 | 73 | >80 | 94 | (2R,2'S)-4b |
|  | Rh2(R/S-DOSP)4 | 71 | 82 | <5 | (±)-4b |
| 4-ClC6H4 | Rh2(S-DOSP)4 | 61 | 79 | 95 | (2S,2'R)-4c |
|  | Rh2(R-DOSP)4 | 58 | 74 | 95 | (2R,2'S)-4c |
|  | Rh2(R/S-DOSP)4 | 54 | 71 | <5 | (±)-4c |
| 3,4-Cl2C6H3 | Rh2(S-DOSP)4 | 56 | 55 | 80 | (2S,2'R)-4d |
|  | Rh2(R-DOSP)4 | 53 | 61 | 81 | (2R,2'S)-4d |
|  | Rh2(R/S-DOSP)4 | 55 | 61 | <5 | (±)-4d |
| 2-naphthyl | Rh2(S-DOSP)4 | 67 | 64 | 70 | (2S,2'R)-4e |
|  | Rh2(R-DOSP)4 | 64 | 60 | 65 | (2R,2'S)-4e |
|  | Rh2(R/S-DOSP)4 | 61 | 57 | <5 | (±)-4e |
| 4-biphenyl | Rh2(S-DOSP)4 | 74 | 71 | 94 | (2S,2'R)-4f |
|  | Rh2(R-DOSP)4 | 75 | 70 | 91 | (2R,2'S)-4f |
|  | Rh2(R/S-DOSP)4 | 74 | 72 | <5 | (±)-4f |

USE OF TETRAHYDROPYRIDINES IN THE TREATMENT OF CENTRAL NERVOUS SYSTEM DISORDERS

This application claims priority to U.S. patent application Ser. No. 60/781,245, filed on Mar. 10, 2006, the entire disclosure of which is incorporated herein by reference.

This work was supported by Grant Nos. NO1 DA-18826 and 5R01DA15225-03 from the National Institutes of Health. The Government has certain rights in the invention.

FIELD OF THE INVENTION

The present invention relates generally disorders of the central nervous system and more particularly to alleviating symptoms of neuropsychiatric disorders.

BACKGROUND OF THE INVENTION

Neuropsychiatric disorders are economically and socially devastating. For example, schizophrenia is the 8th leading cause of disability worldwide with a lifetime prevalence of 0.6 to 1.3% characterized by high morbidity and mortality. Only less than 15% of people with this disability are competitively employed, whilst about 20% live independently. Less than 50% will marry or have a long-term intimate partner.

The domains of pathology in schizophrenia are positive symptoms (delusions, hallucinations, disorganized thoughts and speech, disorganized or bizarre behaviour), negative symptoms (anhedonia, anergia, affective flattening, alogia, avolition-apathy), affective symptoms (dysphoria, hopelessness, suicidality, anxiety, hostility, aggression) and cognitive deficits (speed of information processing, attention, concentration, executive functions, new learning and memory).

The primary effect of first generation antipsychotics is dopamine (D2 receptor) blockade. These are effective in treating positive treatments but minimally effective in treating negative symptoms with common side effects including extrapyramidal symptoms and tardive dyskinesia. The second generation antipsychotics have a lower affinity for dopamine D2 receptors but a higher affinity for serotonin (5HT 1A, 2A, 2C, 3, 6, 7) and nor-epinephrine ($\alpha$1 and $\alpha$2) receptors. While these are effective in treating the positive symptoms of schizophrenia, they exert modest effects on negative symptoms and cognitive deficits. Thus, despite the availability of some drugs for treating neuropsychiatric disorders such as schizophrenia, there are many unmet needs for improved methods and compounds for treating neuropsychiatric disorders.

SUMMARY OF THE INVENTION

The present invention provides a method for using tetrahydropyridine derivatives to alleviate symptoms of neuropsychiatric disorders. The method comprises administering to the individual a tetrahydropyridine derivative in an amount effective to reduce the symptoms of the neuropsychiatric disorder. The compounds can be generally categorized as Ritalin related compounds. Neuropsychiatric disorders presenting symptoms suitable for alleviation according to the present method include but are not limited to broad spectrum psychosis such as schizophrenia and bipolar disorder, depression, mood disorders, addictions, cognitive disorders, and diseases associated with neurodegeneration, such as Alzheimer's disease, Parkinson's disease, and dementia.

In particular embodiments, the compositions administered according to the method of the invention comprise a compound having the general structure:

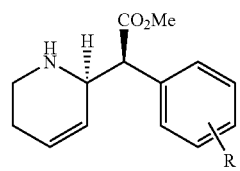

where R represents one or more substituents, such as hydrogen, substituted or unsubstituted phenyls, halogens, and/or adjacent rings which share a side with the R-bearing aryl group.

DESCRIPTION OF THE INVENTION

Figure 1:
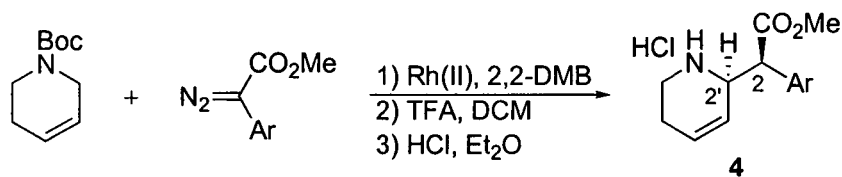
FIG. 1 provides a summary of some examples of compounds synthesized for use in the method of the present invention.

The present invention provides a method for alleviating symptoms of neuropsychiatric disorders. The method comprises administering to an individual a composition comprising a tetrahydropyridine or tetrahydropyridine derivative in an amount effective to reduce the symptoms of the neuropsychiatric disorder.

The method of the invention is suitable for alleviating one or more symptoms of a variety of neuropsychiatric disorders. Individuals with a neuropsychiatric disorder frequently exhibit one or more symptoms that are characteristic of the particular disorder. It is also contemplated that a constellation of symptoms from multiple neuropsychiatric disorders in the same individual can be alleviated by the present method. In this regard, recognizing symptoms from neuropsychiatric disorders, and determining alleviation of said symptoms during or after practice of the present method is well within the purview of a person having ordinary skill in the art and can be performed using any suitable clinical, diagnostic, observational or other techniques. For example, symptoms of schizophrenia include but are not limited to delusions, hallucinations and catatonic behavior. A reduction in any of these particular symptoms resulting from practicing the method of the invention is considered an alleviation of the symptom. Particular neuropsychiatric disorders presenting symptoms suitable for alleviation by the present method include but are not limited to: broad spectrum psychosis such as schizophrenia and bipolar disorder, depression, mood disorders, addictions, cognitive disorders, and diseases associated with neurodegeneration, such as Alzheimer's disease, Parkinson's disease, dementia, and combinations thereof. Symptoms of each of these disorders are well known. Recognizing and determining a reduction in the symptoms of any of these disorders can be readily performed by those skilled in the art.

Compositions comprising an effective amount of the compound may be administered via any conventional route. Such routes include but are not limited to orally, parenterally, intramuscularly, intravenously, mucosally and transdermally. In one embodiment the rout of administration is oral.

Determining a dosage regimen of the compounds is well within the purview of those skilled in the art. By way of example, the dose levels may be from 4 micrograms per kilogram of body weight up to 50 milligrams/Kg of body weight. By way of another example, the dose may be from 20 micrograms/Kg up to 15 mg/Kg. It will be recognized by that dosing parameters, in addition to the weight of the individual, also take into account the age of the individual and the stage of the disease and can be determined according to conventional procedures.

Other components may be combined with the compounds to form pharmaceutical preparations for use in the present method. Such components can be selected depending on factors which include but are not limited to the dosage form, particular needs of the patient, and method of manufacture, among other things. Examples of such components include but are not limited to binders, lubricants, fillers, flavorings, preservatives, colorings, diluents, etc. Additional information regarding pharmaceutical composition components for use with the present method are described in Remington's Pharmaceutical Sciences (18th Edition, A. R. Gennaro et al. Eds., Mack Publishing Co., Easton, Pa., 1990). Accordingly, the selection of particular substances and their compatibilities with the compositions of the present invention can be readily ascertained by those of ordinary skill in the art. Additional details are provided in U.S. Pat. No. 5,763,455, which is incorporated herein by reference.

The tetrahydropyridines and derivatives thereof used in the present method can function as monoamine transporter inhibitors, which have been shown to have significant therapeutic utility in humans. For example, selective serotonin transporter (SERT) inhibitors are some of the most widely used antidepressants. Non-selective ligands which bind to SERT as well as to the norepinephrine transporter (NET) have also been launched as antidepressant agents. Dopamine transporter (DAT) inhibitors are used for the treatment of Attention Deficit Disorders (although DAT inhibitors, such as cocaine, can have abuse potential). Thus, monoamine transporter inhibitors have recognized effects in humans.

In general, and without intending to be bound by any particular classification, the tetrahydropyridines and their derivatives useful in the method of the invention can be broadly categorized as Ritalin related compounds. Specifically, threo-methylphenidate (1) in its racemic form is sold under the trade-name Ritalin. The present method comprises the use of Ritalin related compounds that are erythro unsaturated structures (2).

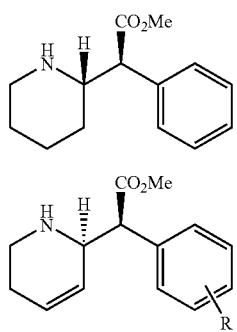

We have determined here that compounds of formula 2 above exhibit favorable biological activity in in vitro pharmacological receptor studies, as well as in an animal model of a neuropsychiatric disorder.

We also describe the synthesis of N-Boc-tetrahydropyridine (4a) by a C—H activation step. This reaction preferentially forms the eyrthro product with reasonably high diastereo- and enantioselectivity.

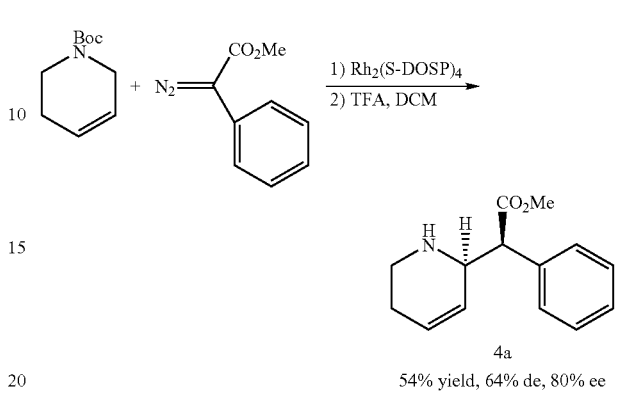

4a
54% yield, 64% de, 80% ee

The synthesis of the compounds was achieved using the general procedure shown above. A variety of methyl aryldiazoacetates were reacted with N-Boc-tetrahydropyridine. The diastereoselectivity of the products range from 57-82% de, and the enantioselectivites were 65-95% ee. FIG. 1 provides a summary of some representative compounds synthesized for use in the method of the present invention. We have found that compounds of formula 2, above, can show favorable biological activity. Accordingly, the compounds of the present invention have the following general structure:

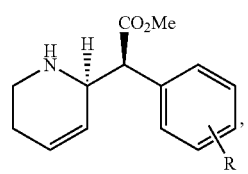

its enantiomer, threo-diastereomer (where the structure is as shown except the dashed bond between the hydrogen and the pyridine ring is directed out of the page instead of into the page) or racemic or diastereomeric mixtures thereof. R can be such that the R-bearing ring is mono-, di- or tri-substituted, and in which the substituents consist of hydrogen, alkyl, alkenyl, alkoxy, halo, nitro, cyano, keto, amino, carboxylate, or a combination thereof. Preferably R represents one or more substituents selected from the group consisting of hydrogen, substituted or unsubstituted phenyls, halogens, and adjacent rings which share a side with the R-bearing phenyl group.

Preferred are substituents such as hydrogen, unsubstituted phenyls, one or more chlorines, bromine, and single adjacent aromatic rings which, together with the R-bearing ring, comprise a naphthyl group.

More preferred are R-groups in the para-position of the R-bearing ring, such as an unsubstituted phenyl in the para position on the R-bearing ring; chlorine substituents at either or both the meta and/or para positions, a bromine substituent at the para position; and one adjacent ring such that, together with the R-bearing ring, it comprises a para-2-naphthyl group. In one embodiment, compound 2 has the structure:

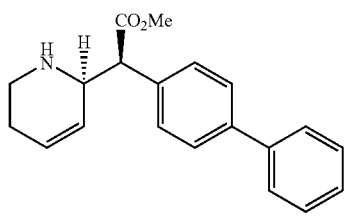

While the present invention is illustrated by way of the following examples, the examples are meant only to illustrate particular embodiments of the present invention and are not meant to be limiting in any way.

Example 1

This Example provides representative experimental procedures for making compounds of the invention.

(S)-Methyl 2-(4-bromophenyl)-2-((R)-1,2,5,6-tetrahydropyridin-2-yl)acetate hydrochloride ((2S,2'R)-4a): Methyl 4-bromo-phenyldiazoacetate (418 mg, 1.6 mmol) in 2,2-dimethylbutane (10 mL) and toluene (4 mL) was added dropwise over 3.5 h using a syringe pump to a solution of $Rh_2(S-DOSP)_4$ (31 mg, 0.016 mmol) and tert-butyl 5,6-dihydropyridine-1(2H)-carboxylate (150 mg, 0.82 mmol) in 2,2-dimethylbutane (10 mL). After the addition was complete, the reaction was stirred for 1 h at 23° C. The solvent was removed under reduced pressure and the residue was redissolved in DCM (15 mL). TFA (0.3 mL, 4.1 mmol) was added and the reaction was stirred for 16 h. The solvent was removed under reduced pressure and the residue was dissolved in $Et_2O$ (30 mL), extracted with 10% HCl (3×15 mL). The combined aqueous layers were basified to pH 8-9 ($NaHCO_3$, 1 M NaOH) and extracted with EtOAc (3×30 mL). The combined EtOAc layers were washed with water (30 mL) and brine (30 mL), then dried over $Na_2SO_4$. The solvent was removed under reduced pressure and a diastereoselectivity of 82% was obtained (as determined by $^1H$ NMR of the crude reaction mixture). The residue was purified by flash chromatography ($SiO_2$, $Et_2O$/Pentane/TEA=50/50/2) to give the free amine. The free amine was then dissolved in $Et_2O$ (20 mL) and HCl (1 M in $Et_2O$, 5 eq) was added. The reaction was stirred for 1 h then the solvent was removed under reduced pressure to give the title compound (2S,2'R)-107 (398 mg, 1.15 mmol, 70% yield) as a white solid. mp=185-186° C.; [a]−74° (c 1.08, $CHCl_3$); FTIR (neat): 2935, 2728, 2699, 1732, 1486, 1434, 1357, 1254, 1165, 1068, 1011 $cm^{-1}$; $^1H$ NMR (500 MHz, free amine, $CDCl_3$) 7.52-7.38 (m, 4H), 6.09-6.01 (m, 1H), 5.65-5.60 (m, 1H), 4.33-4.21 (m, 1H), 3.70-3.59 m, 4H), 3.06-2.97 (m, 1H), 2.92-2.40 (m, 1H), 2.63-2.53 (m, 1H), 2.27-2.23 (m, 1H); $^{13}C$ NMR (75 MHz, $CDCl_3$) 170.6 (C), 132.4 (CH), 131.5 (C), 131.2 (CH), 128.2 (CH), 123.0 (C), 121.9 (CH), 54.5 (CH), 53.1 (CH), 52.8 ($CH_3$), 41.5 ($CH_2$), 21.6 ($CH_2$), N—H proton not observed; LRMS (ESI) m/z (relative intensity): 310 (100); HRMS (ESI) calcd for $C_{14}H_{17}BrNO_2$ ($MH^+$—HCl): 310.0437. Found: 310.0431.

The above compound (2S,2'R)-107 was converted to the trifluoroacetamide in order to measure the enantiomeric excess. Pyridine (2 drops) and TFAA (2 drops) were added to a solution of the free amine (5 mg) in DCM (1 mL). The reaction mixture was stirred for 3 h. The solvent was removed under reduced pressure and the residue was purified by flash chromatography ($SiO_2$, EtOAc/Pentane=1:9) to give the amide. HPLC analysis (trifluoroacetamide): ee 95% (R,R-Whelk column, 3.0% i-PrOH in hexanes, 0.6 mL/min, λ=254 nm, $t_R$=23.2, minor; 31.2, major).

Example 2

This Example demonstrates receptor binding properties of compositions of the invention. For this Example, binding of at biogenic amine transporters was determined using striatum and frontal cortex dissected from frozen Sprague-Dawley rat brains (Pel-Freez, Rogers, AR). Affinities of analogs at dopamine transport sites were determined by displacement of [$^{125}I$]RTI-55 binding in membranes from rat striatum, using 0.5 mg (original wet weight) of membranes and 10 pM [$^{125}I$] RTI-55. Non-specific binding was determined in the presence of 1 μM WF-23 (analog 3a). Affinities of analogs at 5-HT transport sites were determined by displacement of [$^3H$] paroxetine binding in membranes from rat frontal cortex, using 50 mg (original wet weight) of membranes and 0.4 nM [$^3H$] paroxetine. Non-specific binding was determined in the presence of 10 μM fluoxetine. Binding of analogs at norepinephrine transport sites was determined by displacement of [$^3H$] nisoxetine binding in membranes from rat forebrain, using 0.7 nM [$^3H$]nisoxetine. Non-specific binding was determined in the presence of 1 μM desipramine.

Potencies were calculated from displacement curves using 7-10 concentrations of unlabeled analogs, as analyzed by non-linear curve fitting. Because binding of tropanes at dopamine transporters is generally regarded as multiphasic,[3] potencies in inhibiting [$^{125}I$]RTI-55 binding are reported as $IC_{50}$ values. For [$^3H$]paroxetine and [$^3H$]nisoxetine binding assays, $K_i$ values were calculated using the Cheng-Prusoff equation. All data are mean values±S.E.M. of at least three separate experiments, each of which was conducted in triplicate.

The binding affinities to dopamine (DA), serotonin (5-HT), and norepinephrine (NE) transporters for the series of compounds (4) are presented in Table 1. Structural details of exemplary compounds are presented in FIG. 1.

Compound 4 displayed effective biological activity with good binding affinities to dopamine and norepinephrine transporters. Compounds binding to more than one monoamine transporter have been shown to be effective as antidepressants. Thus, the data presented in Table 1 demonstrates that these tetrahydropyridine derivatives have functional properties consistent with antidepressants that have been demonstrated to be effective in humans.

TABLE 1

| Compound | Ar | $DA^a$ ($IC_{50}$, nM) | 5-$HT^b$ ($K_i$, nM) | $NE^c$ ($K_i$, nM) |
|---|---|---|---|---|
| (2S,2'R)-4b | (p-Br)Ph | 5,340 | ND | ND |
| (2R,2'S)-4b | (p-Br)Ph | 5,590 | ND | ND |
| (±)-4b | (p-Br)Ph | 6,020 | ND | ND |
| (2S,2'R)-4c | (p-Cl)Ph | 5,371 | >10,000 | 391 |
| (2R,2'S)-4c | (p-Cl)Ph | 5,025 | >10,000 | 3310 |
| (±)-4c | (p-Cl)Ph | 6,384 | >10,000 | 1910 |
| (2S,2'R)-4d | (3,4-diCl)PH | 329 | >10,000 | 193 |

TABLE 1-continued

| Compound | Ar | DA[a] (IC$_{50}$, nM) | 5-HT[b] (K$_i$, nM) | NE[c] (K$_i$, nM) |
|---|---|---|---|---|
| (2R,2'S)-4d | (3,4-diCl)PH | 216 | >10,000 | 109 |
| (±)-4e | (3,4-diCl)PH | 1,525 | >10,000 | 167 |
| (2S,2'R)-4f | 2-naphthyl | 864 | 1,960 | 800 |
| (2R,2'S)-4f | 2-naphthyl | 547 | 608 | 323 |
| (±)-4f | 2-naphthyl | 496 | 1,200 | 1,190 |

Example 3

To analyze pharmacological activity, a representative compound 2 was analyzed in radioligand binding assays. For this Example, R of compound 2 is a para unsubstituted phenyl, i.e., compound 2 is:

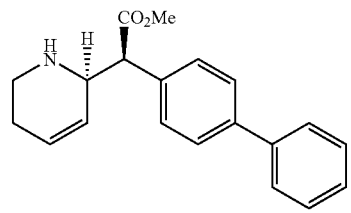

The assays utilized human neuroreceptors and were performed under the experimental parameters set forth in Table 2 using standard techniques. Results of the assays are presented in Table 3.

TABLE 2

| 219600 Dopamine $D_{2L}$ | | 219700 Dopamine $D_{2S}$ | |
|---|---|---|---|
| Source: | Human recombinant CHO cells | Source: | Human recombinant CHO cells |
| Ligand: | 0.16 nM [$^3$H] Spiperone | Ligand: | 0.16 nM [$^3$H] Spiperone |
| Vehicle: | 1% DMSO | Vehicle: | 1% DMSO |
| Incubation Time/Temp: | 2 hours @ 25° C. | Incubation Time/Temp: | 2 hours @ 25° C. |
| Incubation Buffer: | 50 mM Tris-HCl, pH 7.4, 1.4 mM Ascorbic Acid, 0.001% BSA, 150 mM NaCl | Incubation Buffer: | 50 mM Tris-HCl, pH 7.4, 1.4 mM Ascorbic Acid, 0.001% BSA, 150 mM NaCl |
| Non-Specified Ligand: | 10 µM Haloperidol | Non-Specified Ligand: | 10 µM Haloperidol |
| $K_D$: | 0.08 nM* | $K_D$: | 0.09 nM* |
| $B_{MAX}$: | 0.48 pmole/mg Protein* | $B_{MAX}$: | 1.6 pmole/mg Protein* |
| Specified Binding | 85%* | Specified Binding | 90%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |
| 219900 Dopamine $D_{4.2}$ | | 220000 Dopamine $D_{4.4}$ | |
| Source: | Human recombinant CHO-K1 cells | Source: | Human recombinant CHO-K1 cells |
| Ligand: | 0.5 nM [$^3$H] Spiperone | Ligand: | 1.2 nM [$^3$H] Spiperone |
| Vehicle: | 1% DMSO | Vehicle: | 1% DMSO |
| Incubation Time/Temp: | 2 hours @ 25° C. | Incubation Time/Temp: | 2 hours @ 25° C. |
| Incubation Buffer: | 50 mM Tris-HCl, pH 7.4, 1.4 mM Ascorbic Acid, 0.001% BSA, 150 mM NaCl | Incubation Buffer: | 50 mM Tris-HCl, pH 7.4, 1.4 mM Ascorbic Acid, 0.001% BSA, 150 mM NaCl |
| Non-Specified Ligand: | 10 µM Haloperidol | Non-Specified Ligand: | 10 µM Haloperidol |
| $K_D$: | 0.32 nM* | $K_D$: | 0.46 nM* |
| $B_{MAX}$: | 0.55 pmole/mg Protein* | $B_{MAX}$: | 0.63 pmole/mg Protein* |
| Specified Binding | 90%* | Specified Binding | 85%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |
| 220100 Dopamine $D_{4.7}$ | | 220200 Dopamine $D_5$ | |
| Source: | Human recombinant CHO-K1 cells | Source: | Human recombinant CHO cells |
| Ligand: | 1.5 nM [$^3$H] Spiperone | Ligand: | 2 nM [$^3$H]SCH-23390 |
| Vehicle: | 1% DMSO | Vehicle: | 1% DMSO |
| Incubation Time/Temp: | 2 hours @ 25° C. | Incubation Time/Temp: | 2 hours @ 37° C. |
| Incubation Buffer: | 50 mM Tris-HCl, pH 7.4, 1.4 mM Ascorbic Acid, 0.001% BSA, 150 mM NaCl | Incubation Buffer: | 50 mM Tris-HCl, pH 7.4, 1.4 mM Ascorbic Acid, 0.001% BSA, 150 mM NaCl |

TABLE 2-continued

| | | | |
|---|---|---|---|
| Non-Specified Ligand: | 10 µM Haloperidol | Non-Specified Ligand: | 10 µM Flupentixol |
| $K_D$: | 0.48 nM* | $K_D$: | 0.73 nM* |
| $B_{MAX}$: | 0.77 pmole/mg Protein* | $B_{MAX}$: | 0.47 pmole/mg Protein* |
| Specified Binding | 85%* | Specified Binding | 85%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |
| 271650 Serotonin (5-Hydroxytryptamine) 5-$HT_{5A}$ | | 271800, Serotonin (5-Hydroxytryptamine) 5-$HT_{2C}$ | |
| Source: | Human recombinant CHO-K1 cells | Source: | Human recombinant CHO-K1 cells |
| Ligand: | 0.5 nM [$^3$H] Ketanserin | Ligand: | 1 nM [$^3$H] Mesulergine |
| Vehicle: | 1% DMSO | Vehicle: | 1% DMSO |
| Incubation Time/Temp: | 60 minutes @ 25° C. | Incubation Time/Temp: | 60 minutes @ 25° C. |
| Incubation Buffer: | 50 mM Tris-HCl, pH 7.4 | Incubation Buffer: | 50 mM Tris-HCl, pH 7.4, 0.1% Ascorbic Acid, 10 µM Pargyline |
| Non-Specified Ligand: | 1 µM Mianserin | Non-Specified Ligand: | 1 µM Mianserin |
| $K_D$: | 0.2 nM* | $K_D$: | 1.1 nM* |
| $B_{MAX}$: | 0.51 pmole/mg Protein* | $B_{MAX}$: | 4.9 pmole/mg Protein* |
| Specified Binding | 90%* | Specified Binding | 90%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |
| 272200 Serotonin (5-Hydroxytryptamine) 5-$HT_6$ | | 272320 Serotonin (5-Hydroxytryptamine) 5-$HT_7$ | |
| Source: | Human recombinant HeLa cells | Source: | Human recombinant CHO cells |
| Ligand: | 1.5 nM [$^3$H] Lysergic acid diethylamide (LSD) | Ligand: | 5.5 nM [$^3$H] Lysergic acid diethylamide (LSD) |
| Vehicle: | 1% DMSO | Vehicle: | 1% DMSO |
| Incubation Time/Temp: | 2 hours @ 37° C. | Incubation Time/Temp: | 2 hours @ 25° C. |
| Incubation Buffer: | 50 mM Tris-HCl, pH 7.4, 150 nM NaCl, 2 mM Ascorbid Acid, 0.001% BSA | Incubation Buffer: | 50 mM Tris-HCl, pH 7.4, 10 mM $MgCl_2$, 0.5 mM EDTA |
| Non-Specified Ligand: | 5 µM Serotonin (5-HT) | Non-Specified Ligand: | 10 µM Serotonin (5-HT) |
| $K_D$: | 1.3 nM* | $K_D$: | 74 nM* |
| $B_{MAX}$: | 1.7 pmole/mg Protein* | $B_{MAX}$: | 0.95 pmole/mg Protein* |
| Specified Binding | 90%* | Specified Binding | 90%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |
| 220320 Transporter, Dopamine (DAT) | | 204410 Transporter, Norepinephrine (NET) | |
| Source: | Human recombinant CHO-K1 cells | Source: | Human recombinant MDCK cells |
| Ligand: | 0.15 nM [$^{125}$I] RTI-55 | Ligand: | 0.2 nM [$^{125}$I] RTI-55 |
| Vehicle: | 1% DMSO | Vehicle: | 1% DMSO |
| Incubation Time/Temp: | 3 hours @ 4° C. | Incubation Time/Temp: | 3 hours @ 4° C. |
| Incubation Buffer: | 50 mM Tris-HCl, pH 7.4, 100 nM NaCl, 1 µM Leupeptin, 10 µM PMSF | Incubation Buffer: | 50 mM Tris-HCl, pH 7.4, 100 nM NaCl, 1 µM Leupeptin, 10 µM PMSF |
| Non-Specified Ligand: | 10 µM Nomifensine | Non-Specified Ligand: | 10 µM Desipramine |
| $K_D$: | 0.58 nM* | $K_D$: | 0.024 nM* |
| $B_{MAX}$: | 0.047 pmole/mg Protein* | $B_{MAX}$: | 2.5 pmole/mg Protein* |
| Specified Binding | 90%* | Specified Binding | 75%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

TABLE 2-continued

| 274030 Transporter, Serotonin (5-Hydroxytryptamine (SERT) | |
|---|---|
| Source: | Human recombinant HEK-293 cells |
| Ligand: | 0.4 nM [$^3$H] Paroxetine |
| Vehicle: | 1% DMSO |
| Incubation Time/Temp: | 60 minutes @ 25° C. |
| Incubation Buffer: | 50 mM Tris-HCl, pH 7.4, 120 nM NaCl, 5 mM KCl |
| Non-Specified Ligand: | 10 μM Imipramine |
| $K_D$: | 0.078 nM* |
| $B_{MAX}$: | 4.4 pmole/mg Protein* |
| Specified Binding | 95%* |
| Quantitation Method: | Radioligand Binding |
| Significance Criteria: | ≧50% of max stimulation or inhibition |

For Table 3, $IC_{50}$ values were determined by non-linear, least squares regression analysis using Data Analysis Toolbox™ (MDL Information Systems, San Leandro, Calif., USA). Inhibition constants ($K_I$) were calculated using the equation of Cheng and Prusoff (Cheng, Y., et al. *Biochem. Pharmacol.* 22:3099-3108, 1973) using the observed $IC_{50}$ of the tested compound, the concentration of radioligand employed in the assay, and the values for the $K_D$ of the ligand. The Hill coefficient ($n_H$), defining the slope of the competitive binding curve, was calculated using the Data Analysis Toolbox™. Biochemical assay results are presented as the percent inhibition of specific binding or activity unless indicated otherwise. The experiments summarized in Table 3 utilized human dopamine D1, D2 s, D21, D3, D4.2, D4.4, serotonin 5HT1A, 5HT2A, 5HT2C, 5HT6, 5HT7, dopamine transporter (DAT), serotonin transporter (SERT) and the norepinephrine transporter (NET), as indicated in Table 3.

TABLE 3

| Receptors | Concentration | Percentage Inhibition | $IC_{50}$ | $K_i$ | $n_H$ |
|---|---|---|---|---|---|
| Dopamine $D_1$ | 10 μM | 17 | | | |
| Dopamine $D_{2l}$ | 10 μM | 13 | | | |
| Dopamine $D_{2l}$ | 100 μM | 54 | 88.2 μM | 29.4 μM | 0.716 |
| Dopamine $D_{2s}$ | 10 μM | 26 | | | |
| Dopamine $D_{2s}$ | 100 μM | 62 | 51.8 μM | 18.7 μM | 0.788 |
| Dopamine $D_3$ | 10 μM | 15 | | | |
| Dopamine $D_{4.2}$ | 100 | 79 | 50.5 μM | 19.7 μM | 1.76 |
| Dopamine $D_{4.4}$ | 100 | 62 | 66.7 μM | 18.5 μM | 1.01 |
| Serotonin $5HT_{1A}$ | 10 μM | 13 | | | |
| Serotonin $5HT_{2A}$ | 1 μM | 61 | 0.797 μM | 0.228 μM | 1.02 |
| Serotonin $5HT_{2A}$ | 10 μM | 94 | | | |
| Serotonin $5HT_{2C}$ | 10 μM | 52 | | | |
| Serotonin $5HT_{2C}$ | 30 μM | 70 | 13.4 μM | 7.03 μM | 1.12 |
| Serotonin $5HT_6$ | 100 μM | 53 | 94.5 μM | 43.9 μM | 1.12 |
| Serotonin $5HT_7$ | 30 μM | 53 | 25.8 μM | 14.8 μM | 0.774 |
| Dopamine transporter (DAT) | 10 μM | 33 | | | |
| Dopamine transporter (DAT) | 100 μM | 74 | 13.8 μM | 11 μM | 1.3 |
| Serotonin transporter (SERT) | 10 μM | 48 | | | |
| Serotonin transporter (SERT) | 30 μM | 70 | 14.3 μM | 2.33 μM | 1.24 |
| Norepinephrine transporter (NET) | 10 μM | 51 | 10 μM | 9.94 μM | 1.1 |

Thus, a compound having the structure of compound (2), wherein R is an unsubstituted para phenyl, and wherein the compound has the following structure:

can inhibit a variety of ligands from binding to a variety of human neuroreceptors.

Example 4

This Example demonstrates the in vivo efficacy of the presently claimed compositions in reducing symptoms of neuropsychiatric disorders. The efficacy of the compositions is demonstrated using a mouse model described in U.S. Pat. No. 5,723,719, the description of which is incorporated herein by reference. Briefly, the chakragati (ckr) mouse model is a transgenic mouse which exhibits motor activity and social behaviors characteristic of schizophrenia. The mouse also presents lateral ventricular enlargement, which may mirror neuropathological observations in shizophrenia. Atypical antipsychotics clozapine and olanzapine have been shown to reduce the characteristic circling behavior of the mice (Torres et al. (2004) Brain Res. Bull., Vol. 62, 315-326). We have further validated this model by testing risperidone, clozapine, haloperidol and pimozide in the ckr mouse. The behavioral output was assayed by measuring the rate of hyperactivity and circling after administration. The results demonstrated a dose-dependent attenuation of hyperactivity in ckr mice for risperidone, clozapine, haloperidol and pimozide in concentrations relevant to human clinical use. Thus, the ckr mouse model is further demonstrated herein to be valid for evaluation of compounds for use in reducing the symptoms of neuropsychiatric disorders in mammals, including humans.

To obtain the ckr mouse model presented in this Example, a representative compound 2 as set forth in Example 3 was used to investigate a standard measure of sensorimotor gating of the startle reflex. Sensorimotor gating of the startle reflex was assessed via measures of prepulse inhibition (PPI), which is the reduction in startle magnitude when the startling stimulus is preceded immediately by a weak prepulse. This measurement is valuable because the relative loss of PPI has been established in inherited neurodevelopmental disorders, such as schizophrenia in humans, as well as in rats after treatment with certain classes of drugs, including serotonin (5-HT) agonists. In animal models, the PPI test is considered to have good face, predictive and construct validity for sensorimotor gating deficits in schizophrenia.

In order to assay the effect of the compositions of the present invention in the ckr model, experiments were performed as follows:

Drug Solutions

A stock solution of compound 2 was dissolved in DMSO, and then diluted to 10 mg/10 ml with distilled water such that the final concentration of DMSO was 0.5%. Each animal received 10 mg/kg of the test drug in a volume of 0.1 ml per 10 g. Additional drugs were tested in parallel in a similar manner.

Motor Activity

Twenty ckr mice (male and female, 3 months old) were randomly assigned to receive the test drug (compound 2) or 0.5% DMSO vehicle. The drug was tested in 5 mice. Each treatment was separated by a minimum washout period of 3 days. On the day of testing, mice were brought into the behavioral test room and allowed to acclimatize for at least 1 hour. They then received intraperitoneal injections of the 0.1 ml/10 g (10 mg/kg) of the test drug solution or vehicle. They were returned to their cage and 20 minutes later they were placed in a 190 mm diameter, 300 mm deep circular recording chamber. Four mice were tested simultaneously in 4 separate chambers. Between each testing session the chambers were wiped down with 70% ethanol and allowed to dry for at least 10 min. The mice were monitored with an overhead video camera for 15 minutes. Their behavior was videotaped and simultaneously digitized and tracked (Ethovision Version 2, Noldus). The total distance moved, the velocity of movement, and the time spent moving were calculated. Each treatment was separated by a minimum washout period of 3 days.

Apparatus

Startle reactivity was measured using a startle chamber (SR-LAB, San Diego Instruments, San Diego, Calif.). The chamber consisted of a clear plexi-glass cylinder resting on a platform inside a ventilated, sound-attenuating chamber. A high frequency loudspeaker inside the chamber produced both a continuous background noise of 65 dB as well as the various acoustic stimuli. Vibrations of the plexi-glass cylinder, caused by the whole body startle response of the animals, were transduced into analog signals (0 to 5,000 mV range) by a piezoelectric unit attached to the platform. These signals were then digitized for analysis.

Procedure

The protocol for measuring PPI was adapted from known techniques. There were 8 mice in each group. The mice were acclimatized for 60 mins in the behavioural test room prior to measurement of PPI. They were then placed in the plexi-glass cylinder and exposed to 65 dB background white-noise. After 5 mins, the mice were exposed to a series of 5 different types of trials involving exposure to pulses of white-noise: (1) pulse-alone trials, during which a 120 dB stimulus was presented for 40 ms; (2)+3 dB pre-pulse trials, during which a 20 ms, 68 dB (+3 dB above 65 dB background) pre-pulse preceded the 120 dB pulse by the pre-pulse to pulse interval; (3)+6 dB pre-pulse trials, during which a 20 ms, 71 dB (+6 dB above 65 dB background) pre-pulse preceded the 120 dB pulse by the pre-pulse to pulse interval; (4)+12 dB pre-pulse trials, during which a 20 ms, 77 dB (+12 dB above 65 dB background) pre-pulse preceded the 120 dB pulse by the pre-pulse to pulse interval; and (5) no pulse trials. For the measurement of differences in PPI between the wild-type, heterozygous and ckr mice, the pre-pulse to pulse interval was set at 100 ms. A characteristic of pre-pulse inhibition is that the phenomenon disappears at very short pre-pulse to pulse intervals. In the ckr mice, the protocol was subsequently repeated with 25 ms, 100 ms, and 175 ms pre-pulse to pulse intervals in pseudorandom order to confirm that the effect seen was a pre-pulse inhibition. In one session, a total of 52 trials were conducted in pseudorandom order: 20 pulse alone trials, and 8 each of the other four trials. These were preceded by 4 pulse alone trials, which were discarded. The average inter-trial interval was 15 s (9-21 s range). The startle response was recorded as the average movement detected over 65 ms following the pulse. Cases were the startle response amplitude on the pre-pulse trial exceeded 90% of the average startle response amplitude on the pulse alone trials were excluded.

The startle amplitude was measured as the average startle response for the pulse-alone trials. Pre-pulse inhibition was calculated as percentage PPI, namely as $(A-B)/A \times 100$, where A was the average startle response amplitude on pulse-alone trials and B was the average startle response amplitude on pre-pulse trials. Use of this measure, in preference to absolute difference scores, minimizes the possible effects of individual differences in startle amplitude on PPI (Mansbach et al., (1988) *Neuropsychopharm.* Vol. 2, pp 299-308).

The overall effect of compound 2 resulted in a trend towards decreased velocity. Compound 2 significantly decreased the time spent moving and resulted in a trend of increased PPI over the control across all pre-pulse intensities. Thus, compound 2 is demonstrated in this Example to be effective at reducing the symptoms of a model neuropsychiatric disorder.

Example 5

This Example a computer program (in silico) comparison of compound 2 as set fort in Example 3 to the following antipsychotic drugs: Chlorpromazine (Thorazine); Fluphenazine (Prolixin); Perphenazine (Trilafon); Prochlorperazine (Compazine); Thioridazine (Mellaril); Trifluoperazine (Stelazine); Haloperidol (Haldol); Droperidol and Pimozide (Orap).

All these compounds are general dopamine antagonists, and specifically dopamine D2 antagonists. None are dopamine uptake inhibitors. Compound 2, in contrast, is a Dopamine uptake inhibitor. All the major antipsychotics listed are hERG potassium channel antagonist and Alpha adrenoreceptor antagonist with exception of Haloperidol (Haldol). hERG affinity is often, though sometimes unpredictably, linked to arrhythmogenesis. In-silico studies with Compound 2 as set forth in Example 3 indicate it does not interact with the hERG or Alpha adrenoreceptor. Thus, the antipsychotic properties of this compound are novel compared to the comparator compounds and it is likely to lack some of the side-effects of the listed antipsychotics.

Compound 2 also shows antidepressant binding patterns. Compounds used for comparison included: Venlafaxine (Effexor) Citalopram (Celexa) Paroxetine (Paxil/Seroxat) Bupropion (Wellbutrin) Fluoxetine (Prozac/Sarafem) Sertraline (Zoloft), Doxepin and Sulpiride (also an antipsychotic). Almost all these drugs are 5-Hydroxytryptamine uptake inhibitors. Most are also dopamine uptake inhibitors (e.g. Doxepin, Sertraline, Bupropion, Venlafaxine). Thus, in-silico studies indicate compound 2 also has antidepressant properties.

From the foregoing analysis of compound 2, and without intending to be bound by any particular theory, the following observations can be made.

The high level 5-HT2$_A$/5-HT2$_C$ antagonism would make compound 2 clozapine or olanzapine-like. The 5-HT2$_A$/5-HT2$_C$ block being even higher relative to DA receptors than for clozapine and olanzapine, this compound may have stronger mood stabilizing effects and even less extrapyramidal side effects than current therapies.

The ratio of DA D$_2$ to D$_1$ receptor is good and makes this drug more risperidone-like and may reduce extrapyramidal effects. As a potential antipsychotic, the ratio of D$_{2S}$ to D$_{2L}$ is good and may make this drug more clozapine-like and therefore more effective against sensorimotor gating (PPI) deficits and less likely to have extrapyramidal side effects.

The relatively strong SERT and DAT activity is novel. It is considered that this may make the drug better for mood-stabilization or presentation of schizophrenia combined with mood disorders. It may also help to reinstate DA activity at other DA receptor subtypes blocked less by the drug—for example D$_1$, D$_4$ or D$_5$ in the prefrontal cortex, helping to restore cognitive function. As a potential antidepressant, secondary indications in migraine, hypertension (especially stress-related), and treatment of addiction come to mind.

Our in vitro binding assays presented herein for compound 2 as set fort in Example 3 indicated that this compound is a dopamine D$_2$ receptor antagonist. This is consistent with an antipsychotic profile of activity. Independent in silico comparisons to first generation, typical antipsychotics have confirmed that the affinity profile of compound 2 does not match that of typical antipsychotics which bind with higher affinity to D$_2$ receptors and cause extrapyramidal side effects. The newer, atypical antipsychotics produce fewer extrapyramidal side effects. Consistent with an atypical antipsychotic profile, compound 2 has high affinity at 5-HT$_2$ receptors, particularly the 5-HT$_{2A}$ receptor. Like olanzapine and clozapine, compound 2 also has 5-HT$_{2C}$ and 5-HT$_6$ receptor antagonism. Antagonism at these receptors is predicted to enhance mood stabilizing effects and to offer advantages in the amelioration of cognitive dysfunction. In silico predictive analysis and in vitro binding assays have independently identified that compound 2 has a profile of inhibition of noradrenaline, dopamine and 5-HT reuptake that is unique among antipsychotics. This profile of binding indicates that compound 2 will have additional mood stabilizing, antidepressant, and precognitive effects and is likely to be particular efficacy in psychosis with depression and amelioration of cognitive dysfunction. This pattern of activity also suggests efficacy in depression and bipolar disorder.

As noted above, in silico analysis also predicts that compound 2 does not interact with the hERG channel and so does not have the associated risk of drug-induced cardiac arrhythmia and sudden death shared by many of the current antipsychotics and antidepressants. Additionally, the in silico analysis did not predict any interaction with histamine receptors, suggesting that compound 2, unlike current atypical antipsychotics is unlikely to cause sedation, weight gain and associated drug-induced diabetes.

Affinity of compound 2 compares reasonably with the atypical antipsychotic clozapine and would not be predicted to be problematic as there is not indication of toxicity that would prevent administration at appropriate doses to achieve adequate receptor and transporter blockade.

The foregoing description of the specific embodiments is for the purpose of illustration and is not to be construed as restrictive. From the teachings of the present invention, those skilled in the art will recognize that various modifications and changes may be made without departing from the spirit of the invention.

REFERENCES (1) Davies, et al. *J Am. Chem. Soc.,* 1999, 121, 6509-6510
(2) Davies, et al. *Biorg. Med. Chem. Lett.* 2004, 14, 1799.
(3) Madras, et al. *Pharmacol. Exp. Ther.* 1989, 251, 132.
(4) Cheng, et al. *Biochem. Pharmacol.* 1973, 22, 3099.

We claim:

1. A method for alleviating one or more symptoms of a neuropsychiatric disorder in an individual, wherein the neuropsychiatric disorder is schizophrenia, the method comprising administering to the individual a composition comprising a compound in an amount effective to alleviate the symptoms of the neuropsychiatric disorder, wherein the compound has the following structure (2):

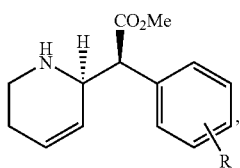

its enantiomer, or racemic mixtures thereof; wherein R can be such that the R-bearing ring is mono-, di- or tri-substituted, and in which the substituents consist of hydrogen, alkyl, alkenyl, alkoxy, halo, nitro, cyano, keto, amino, carboxylate, or a combination thereof, and wherein the administration of the composition alleviates one or more symptoms of the neuropsychiatric disorder.

2. The method of claim 1 wherein R is one or more substituents selected from the group consisting of hydrogen, substituted or unsubstituted phenyls, halogens, and adjacent rings which share a side with the R-bearing phenyl group.

3. The method of claim 1, wherein R is a p-bromo.

4. The method of claim 1, wherein R is a p-chloro.

5. The method of claim 1, wherein R is an unsubstituted p-phenyl.

6. The method of claim 1, wherein R consists of chlorine substituents at positions 3 and 4.

7. The method of claim 1, wherein R is a p-2-naphthyl.

8. A method for alleviating one or more symptoms of a neuropsychiatric disorder in an individual, wherein the neuropsychiatric disorder is schizophrenia, the method comprising administering to the individual a composition comprising a compound in an amount effective to alleviate the symptoms of the neuropsychiatric disorder, wherein the compound has the threo-diasteromeric structure of following structure (2):

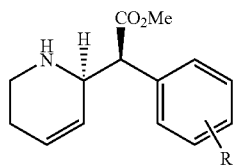

or a diastereomeric mixture of said threo-diastereomer and its erythro diastereomer; wherein R can be such that the R-bearing ring is mono-, di- or tri-substituted, and in which the substituents consist of hydrogen, alkyl, alkenyl, alkoxy, halo, nitro, cyano, keto, amino, carboxylate, or a combination thereof, and wherein the administration of the composition alleviates one or more symptoms of the neuropsychiatric disorder.

9. The method of claim 8 wherein R is one or more substituents selected from the group consisting of hydrogen, substituted or unsubstituted phenyls, halogens, and adjacent rings which share a side with the R-bearing phenyl group.

10. The method of claim 8, wherein R is a p-bromo.

11. The method of claim 8, wherein R is a p-chloro.

12. The method of claim 8, wherein R is an unsubstituted p-phenyl.

13. The method of claim 8, wherein R consists of chlorine substituents at positions 3 and 4.

14. The method of claim 8, wherein compound 2 is:

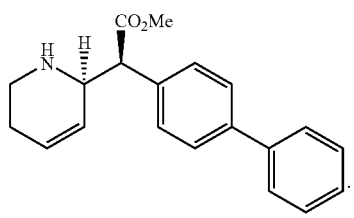

15. The method of claim 1, wherein the composition further comprises a pharmaceutically acceptable carrier.

16. The method of claim 8, wherein the composition is administered via a route selected from the group consisting of orally, parenterally, intramuscularly, intravenously, mucosally and transdermally.

17. The method of claim 8, wherein the composition is administered orally.

* * * * *

UNITED STATES PATENT AND TRADEMARK OFFICE
CERTIFICATE OF CORRECTION

| | | |
|---|---|---|
| PATENT NO. | : 7,851,487 B2 | Page 1 of 1 |
| APPLICATION NO. | : 11/716815 | |
| DATED | : December 14, 2010 | |
| INVENTOR(S) | : Davies et al. | |

It is certified that error appears in the above-identified patent and that said Letters Patent is hereby corrected as shown below:

Title page, item (*), the sentence

"This patent is subject to a terminal disclaimer."

should be deleted.

Signed and Sealed this
Thirty-first Day of July, 2012

David J. Kappos
*Director of the United States Patent and Trademark Office*